United States Patent [19]

Ruby

[11] 4,050,461
[45] Sept. 27, 1977

[54] STOMA IRRIGATION SYSTEM
[76] Inventor: Max H. Ruby, 170 Hillside Ave., Waterbury, Conn. 06710
[21] Appl. No.: 679,672
[22] Filed: Apr. 23, 1976
[51] Int. Cl.² .............................................. A61M 3/00
[52] U.S. Cl. ..................................... 128/227; 128/283
[58] Field of Search ............... 128/283, 227, 247, 248, 128/251, 239, 245, 242, 224, 225

[56] References Cited
U.S. PATENT DOCUMENTS

| 228,422 | 6/1880 | Turner | 128/239 |
|---|---|---|---|
| 2,366,059 | 12/1944 | Schunk | 128/283 |
| 2,902,036 | 9/1959 | Perry | 128/283 |
| 3,398,744 | 8/1968 | Hooper | 128/283 |
| 3,910,274 | 10/1975 | Nolan | 128/283 X |
| 3,916,897 | 11/1975 | Elmore et al. | 128/283 X |

FOREIGN PATENT DOCUMENTS 774,904 1/1968 Canada ................................ 128/283

Primary Examiner—Ronald L. Frinks
Assistant Examiner—Michael H. Thaler
Attorney, Agent, or Firm—St. Onge, Mayers, Steward & Reens

[57] ABSTRACT

A stoma irrigation device is disclosed which enables a colostomy patient to adapt a simple open-ended tubular sheet plastic drain sleeve of low cost, disposable type for use in performing any of the several standard methods of irrigation using a cone, a catheter, or combination of cone-and-catheter under "closed system" conditions.

2 Claims, 7 Drawing Figures

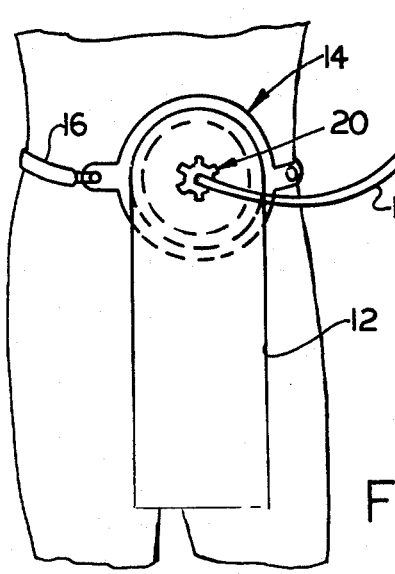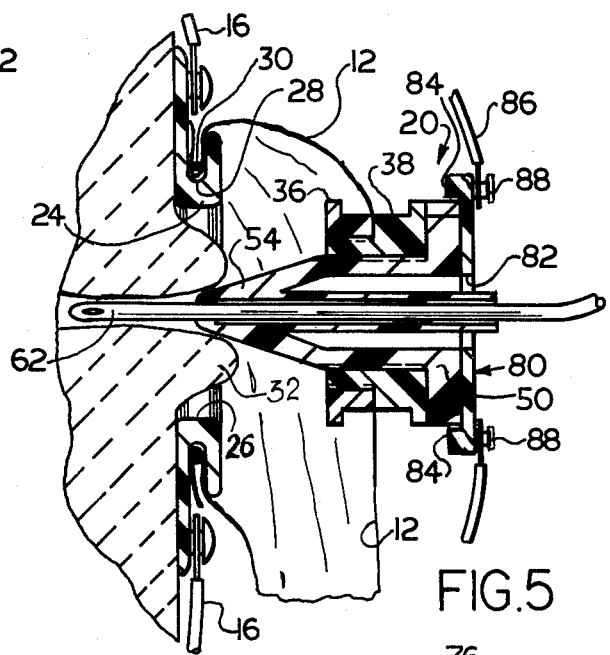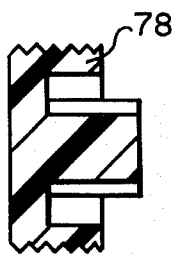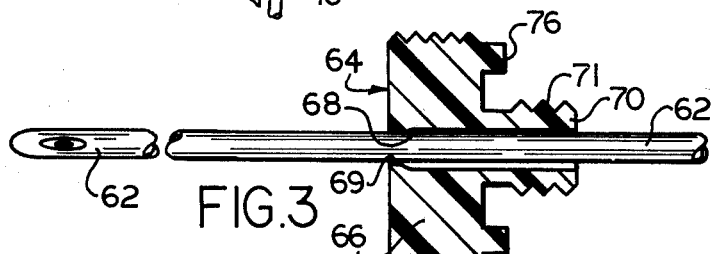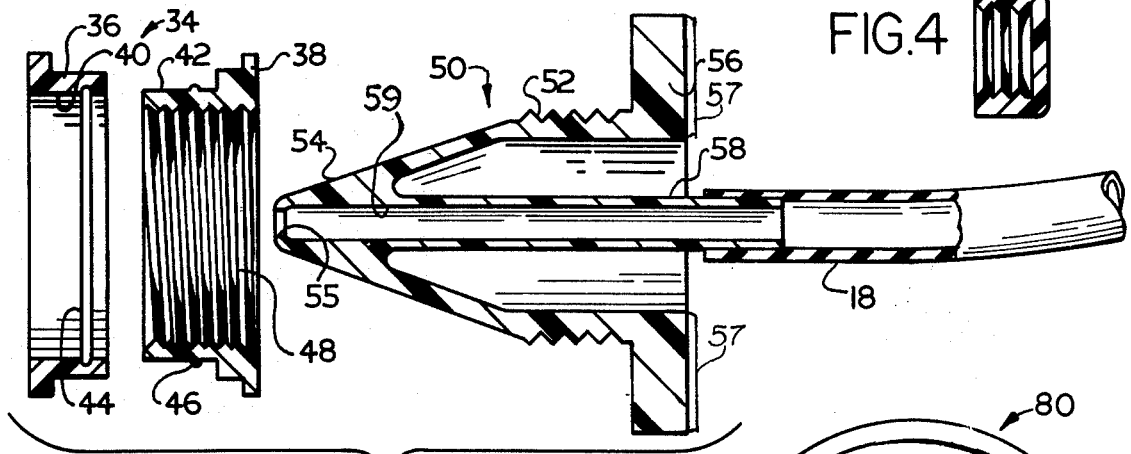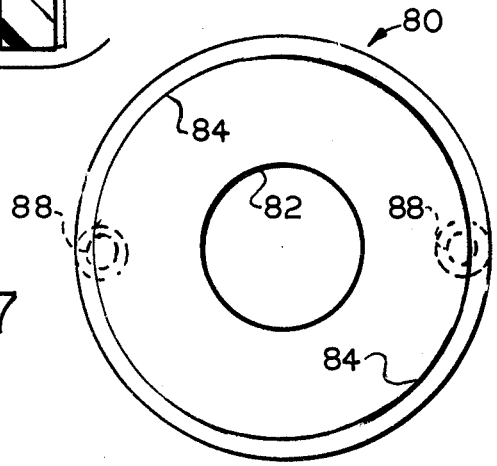

STOMA IRRIGATION SYSTEM

BACKGROUND OF THE INVENTION

This invention pertains to post-surgical devices for colostomy patients to facilitate regular irrigation of the bowel through a stoma opening.

Patients who have had the lower portion of the bowel, including the rectum, removed surgically, require a new opening for elimination of waste matter. The new artificial opening, or stoma, made on the abdominal wall into the large bowel and termed a colostomy, has no voluntary sphincter control by the patient. In order to avoid involuntary bowel movement through the stoma, it is customary and desirable for the patient periodically to take an enema, commonly called irrigation, through the stoma. The frequency required of this irrigation is generally daily, or perhaps every second day, in order to keep the bowel free from involuntary discharges.

In general, the irrigation system employed consists of a water reservoir and means for suspending it at about shoulder level to supply gravity flow of the water through a tube leading from the reservoir to the stoma. A sheet plastic sleeve is adapted to be attached to the patient by a plate member and supporting belt, and the sleeve has provision at or near its upper end for encompassing the stoma of the patient and making a fluid tight engagement with the abdominal wall to protect the patient from spilling or soiling. The lower end of the sleeve is open for discharge of the irrigation fluid and waste into a toilet or other receptacle. Provision is made at the upper end of the sleeve for ducting the irrigating fluid through the sleeve and into the stoma. In general there are two types of sleeves available to the patient, one or the other of which is selected in accordance with whether the patient employs the so-called open method or closed method of irrigation.

Sleeves adapted for use in the open method are supplied to the patient with the axially upper end left open, as well as the lower end, and are provided with a lateral opening in the sleeve wall a short distance below its open upper end. The open upper end permits the patient to insert his hand into the top of the sleeve for manipulation of the catheter or cone during insertion into the stoma, preparatory to irrigation. Some form of closure means, such as a clip or other device, is employed to close the upper end of the sleeve when the cone or catheter tube is withdrawn after the irrigating fluid has entered the bowel through the stoma. The sleeve, with its lateral opening in registration with the stoma, is held in place on the patient by an annular body frame or plate secured by a belt about the patient's waist. One such open method system is shown in U.S. Pat. No. 3,910,274, FIG. 3.

In the closed system, the lower end of the sleeve is open as before, but the axially upper end is closed by being secured about the opening of the body frame that encompasses the stoma area. Alternatively, the axially upper open end of the sleeve may be closed by a weld seam, in which case a lateral opening must be provided in it for attachment to the body frame.

The introduction of the irrigation fluid into the stoma is made by means either of a soft flexible catheter tube, or by means of a smooth cone. In the closed method, the catheter may be passed through a suitably small hole in the outer wall of the sleeve, in registry with the plate opening surrounding the stoma. Some form of seal or flap is provided at the catheter hole to prevent the irrigating fluid from escaping through the hole in the sleeve on return of the fluid at the completion of the irrigation. Such arrangements are shown, for example, in U.S. Pat. Nos. 2,154,202, 2,504,872, 2,902,036, 2,928,393 and 3,292,625.

Where, however, it is desired to use a cone rather than a catheter tube, a much longer opening is required in the outer wall of the sleeve, and the closure or sealing methods employed for catheters is not satisfactory or practical for cones, principally because of the difficulty in providing a large opening with tight closure to prevent leakage. Suggestion has been made to incorporate a cone integrally with a sleeve in order to permit use of the closed system of irrigation and also to avoid leakage around the cone where it passes through the sleeve. See U.S. Pat. No. 3,830,235. However, use of the cone has heretofore generally necessitated use of the open method of irrigation, with its attendant disadvantages. These include possible spilling, splashing and soiling by inadvertent escape of the irrigating fluid or waste discharge at the open upper end of the sleeve before it has been closed off after removal of the cone. Closing of the sleeve requires some form of clip or equivalent device, and the attachment of these on the sleeve can present a practical problem of manual dexterity for a patient.

Many of the irrigation sets now available are designed only for use in the open method with a plastic sleeve which is meant to be rinsed clean after each irrigation, dried and re-used repeatedly. Apart from the problems of maintaining this equipment sanitary, reusable sleeves are inherently more expensive than single-use, disposable plastic ones.

Until several years ago, only the catheter method of irrigation through the stoma was available, and thousands of patients still use this method. More recently the cone method has been supplanting the catheter because of its many advantages, more especially avoidance of bowel injury and more efficient irrigation performance. Some patients with obese abdominal walls, or with redundant tissue at the stoma, have difficulty in inserting the cone to a sufficient depth. In these cases, use of the cone supplemented by a catheter extension to provide an inch or so of catheter projecting from the cone is an advantage.

Irrigation by the closed method generally is more comfortable for a patient and gives greater peace of mind. As mentioned above, this system is easily adaptable to a catheter or rectal tube by providing a small opening in the outer sleevewall in registry with the stoma opening, but no satisfactory arrangement has heretofore been provided for use of a cone under the conditions imposed by the closed upper end of the sleeve. It may often be desirable, moreover, for the patient to select between use of the catheter, cone, or combination of the two, and the prior irrigation systems have not afforded such flexibility.

SUMMARY OF THE INVENTION

The present invention provides improvement in the method of and apparatus for irrigating the bowel of a colostomy patient through an abdominal stoma, employing the closed system. A low-cost, single-use, disposable plastic sleeve is made capable of use in the closed system by provision of a cone-catheter-coupling device or adapter set of novel construction. The adapter set permits a patient to choose different methods of irrigation, since one method may not be the best for all patients. The components of the adapter set are easily assembled to an open-ended sleeve, and are likewise easily removed and cleaned after use. With the adapter set, a peripherally sealed access port is readily formed by the patient in a wall of the sleeve, and various closure members comprising a cone, catheter, combination of the two, or a sealing plug are receivable in the port to accommodate different modes of use. The adapter set is designed for easy fabrication by known plastic molding techniques using suitable resins, such as polyethylene. An additional, optional feature of the invention is the provision of a circular retention plate for assisting the body frame in supporting the device on the patient. The retention plate fits over the base flange of the cone to maintain engagement of the cone in the stoma without requiring the patient to hold it manually in position.

A preferred embodiment of the invention is illustrated in the accompanying drawings and described in detail hereinafter. It will be apparent from the disclosure herein that various modifications in the details of the specifically shown components may be made without departing from the inventive concept, and the following description is intended to be illustrative, not limiting, of the invention.

In the drawings:

FIG. 1 is a fragmentary perspective view showing generally the manner of attachment of the irrigating equipment to the body of a colostomy patient;

FIG. 2 is an exploded view in cross section of the adapter set incorporating the cone closure member;

FIG. 3 is a view, partly in section, of a catheter tube and catheter-accepting closure member for use in conjunction with the adapter;

FIG. 4 is a sectional view in side elevation of a cap for the closure member of FIG. 3;

FIG. 5 is a cross sectional view showing the adapter set incorporating a cone-and-catheter combination;

FIG. 6 is a cross sectional view of a closure plug for the adapter; and

FIG. 7 is a plan view of a body plate for supplemental support of a cone in the stoma opening of the patient.

DETAILED DESCRIPTION OF THE PREFERRED EMBODIMENT

The general arrangement involving the use by a patient of a stoma irrigating system is shown in FIG. 1, wherein a plastic waste sleeve 12 is attached to a body plate 14 supported in position against the abdominal wall of the patient by a suitable belt 16. An irrigating fluid duct 18 delivers water by gravity from a reservoir (not shown) to the stoma opening in the body plate, passage through the outer wall of sleeve 12 being accomplished by adapter set 20 of the present invention. A quick disconnect 22 is provided in duct 18 between the irrigating device and the irrigation fluid reservoir to enable the patient to break the connection to the reservoir for substitution of different components; e.g. cone, catheter, etc. Conventional shutoff means (clamp, petcock, etc.) is provided in the duct above the disconnect to reduce or stop the flow of fluid from the reservoir.

Further details of the manner of attaching the irrigation device to the stoma of a patient are shown in FIG. 5. Plastic sleeve 12, which may be made of any suitable thin plastic such as polyethylene sheet, is formed into a simple open-ended tube which is attached by its upper end to body frame 14. While other available arrangements could be used, the illustration in FIG. 1 represents a particularly suitable type of body frame with belt attachment. In this instance, the open end of the sleeve is simply placed over a raised resilient annular boss 24 defining the stoma-receiving opening 26 of the body frame. Boss 24 is formed with an external peripheral groove 28 to accept the mouth of the sleeve and to retain it in water-tight relation to the plate, as by means of an elastic band 30. When properly positioned on the patient by the belt, the opening of the body plate encompasses the patient's stoma 32, forming a peripheral seal on the surface of the patient's abdomen.

In order to gain access for the irrigating device through the outer wall of a plastic sleeve 12, an adapter set 20 is provided which includes a coupling 34 comprising a pair of axially interengageable annular members 36, 38. As seen more particularly in FIGS. 2 and 5, member 36 is adapted to be positioned interiorly of the outer wall of sleeve 12, while member 38 is disposed externally of that wall. This arrangement could be reversed. The diameter of internal wall 40 is adapted to receive external wall 42 with an axially interengageable friction fit designed to accommodate the interpositioning of the wall of sleeve 12, yet to form a fluid-tight seal about the encompassed section of the wall. See more particularly FIG. 5. Complementary annular groove 44 and rib 46 frictional interference elements are provided on members 36, 38, respectively, which elements are engageable by straight axial movement of said annular members at their fully interfitted condition, and when so engaged the frictional interference elements insure retention of the members in axially interfitted position and the formation of an effective seal with the wall of sleeve 12. The complementary rib and groove elements produce a snap-fit when engaged or disengaged, further assuring the maintenance of an effective seal. The radially inner member 38 is also formed on its inner wall with suitable threads 48 or equivalent fastening means. Member 38 accordingly is adapted to receive and retain any of several different accessory closure members to enable coupling 34 to function in any of several different methods of stoma irrigation. As seen in FIG. 2, a stoma cone 50 is adapted to be threaded into member 38, after of course cutting away the circular section of wall of sleeve 12 encompassed by the coupling unit 34. To this end, stoma cone 50 is formed with complementary threads 52 adjacent the exterior of its base for engagement with threads 48 of member 38. The assembled condition of the cone and coupling unit is illustrated in FIG. 5. Cone 50 is formed with an apical portion 54 which projects from the threaded base portion 52 so as to extend inwardly of coupling 34 when assembled therewith, thereby enabling the apical portion to be introduced into the stoma opening of the patient. Cone 50 is provided with a peripheral flange 56 at its base having raised, radial spokes or ribs 57 which provide a convenient means for tightening the cone into and removing it from the coupling 34. Placement of the cone into the stoma is facilitated by the flange of the cone, serving as a convenient external grip for this. Cone 50 is formed with an axial passage 59 which opens onto the apex of the cone, and rearwardly thereof is defined by an internal tube 58 which terminates outwardly of base flange 56 of the cone. The tube 58 is designed to receive the usual irrigation tubing 18.

The arrangement illustrated in FIG. 3 consists of a standard catheter tube 62 which is received in a catheter plate 64. This assembly is adapted to be screwed into coupling 34 in place of the stoma cone 50 when the patient desires to employ the catheter method of irrigation. Catheter plate 64 is sized to fit in member 38 of the coupling unit, and to that end is provided with complementary threads 66 on its periphery. Plate 64 is formed with an axial duct or channel 68 which extends from the inner face of the plate through a rearwardly projecting nipple 70. The terminal end 69 of duct 68 is reduced to make an exact fit with catheter tube 62, forming a sliding seal that permits the catheter to be introduced to the desired length without causing a leak. The external wall of nipple 70 of the catheter plate may be threaded at 71 to receive a closure cap 72, or plug, after withdrawal of the catheter tube. In order to facilitate connecting and disconnecting catheter plate 64 in respect to coupling member 38, the plate is formed on its external base with spaced lugs or ears 76 to provide a finger grip accessible to the patient.

In FIG. 5, there is illustrated a further functional arrangement for the irrigating system which may be desirable for use by certain patients. This comprises a combination of the cone and catheter accessories. In this arrangement, the internal passage 59 of cone 50 is reduced at its inner end, as at 55, to form a tight, nonsliding fit with catheter 62, thereby holding the extending catheter to a fixed projecting distance.

In FIG. 6, the closure member illustrated is simply a sealing plug 78 which is adapted to be threadedly received in member 38 after the cone or cone with catheter extension are removed and to block the port completely.

An annular cone-retaining plate 80, shown in FIGS. 5 and 7, may be included in the adapter set to provide means for relieving a patient of having to manually hold the stoma cone in engaged position during irrigation. Retaining plate 80 has a central aperture 82 which makes a free fit over the rearwardly projecting tube 58 of the cone so as to allow it to abut against the rear face of the cone. Plate 80 is formed with peripheral flanges 84 which encompass the periphery of cone flange 56, thereby keeping the plate centered on the cone. A belt 86 is attachable to studs 88 on the rear (outer) face of the plate and passes around the patient's waist, similar to belt 16, in order to support the plate in its cone-retaining position.

The various components of this invention are preferably formed of molded plastic, the material of choice being polyethylene although other medically or surgically compatible materials may obviously be employed.

The provision of an adapter set comprising an integrated assembly of a coupling, cone, catheter and plug closure components in accordance with the present invention permits the patient a wide flexibility of choice of different methods of irrigation, enabling him or her to select one most suited, or to experiment in the use of different methods, as may be desired.

The foregoing description of the components comprising the novel adapter set is intended to be illustrative of the inventive concept, and it will be obvious that modifications can be made in the specific form and arrangement of parts within the scope of the apended claims.

What is claimed is:

1. A stoma irrigation device for use with a plastic drain sleeve of tubular configuration, whereby a colostomy patient is enabled to use said sleeve in the cone or combination cone-and-catheter irrigation methods under closed system condition, said device comprising a coupling unit comprising a pair of axially interengageable annular members adapted to be axially slidably interfitted, one within the other from opposite sides of a plastic drain sleeve to encompass a section of the sleeve wall and form a fluid-tight seal about said wall section, one of said annular members being formed with attachment means for coupling a closure member thereto in fluid-tight relation, said annular members including complementary frictional interference elements which are engaged in the fully axially interfitted position of said members to frictionally retain them in such position and also to maintain said seal with the wall of said plastic sleeve; and a closure member adapted to mate with said one annular member and detachably engage said attachment means to form a fluid-tight joint with said annular member after the encompassed section of plastic sleeve wall has been cut away, said closure member comprising a cone which is formed in its apical region to be received in said inner annular coupling member and to project inwardly beyond the inner end of said coupling member, said cone having at its base attachment means for detachably engaging said engagement means of said coupling to cause said apical region to protrude internally of the inner face of said coupling, said cone being formed with a passage extending axially therethrough and being formed with a tube for connection to a source of irrigating fluid.

2. A device as defined in claim 1, wherein said passage extending through the cone is formed interiorly to provide a tight seal with a catheter tube inserted therein.

* * * * *